(12) United States Patent
Rattner

(10) Patent No.: US 6,247,963 B1
(45) Date of Patent: Jun. 19, 2001

(54) CONNECTION UNIT FOR USE IN A MEDICAL WORKPLACE

(75) Inventor: Manfred Rattner, Grossenseebach (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/313,469

(22) Filed: May 17, 1999

(30) Foreign Application Priority Data

May 15, 1998 (DE) ............................................. 198 22 020

(51) Int. Cl.$^7$ ...................................................... H01R 11/00
(52) U.S. Cl. ........................ 439/502; 174/72 A; 248/68.1
(58) Field of Search ........................... 439/502; 248/68.1, 248/74.1; 174/72 A, 135, 136

(56) References Cited

U.S. PATENT DOCUMENTS

| 1,292,716 | * | 1/1919 | Cox | 439/502 |
|---|---|---|---|---|
| 2,997,531 | * | 8/1961 | Oldham et al. | 174/72 A |
| 4,099,626 | * | 7/1978 | Magnussen, Jr. | 248/68.1 |
| 4,494,520 | * | 1/1985 | Hurwitz | 174/72 A |
| 4,874,908 | * | 10/1989 | Johansson | 248/68.1 |
| 5,377,939 | | 1/1995 | Kirma | 248/68.1 |
| 5,816,848 | * | 10/1998 | Zimmerman | 439/502 |

FOREIGN PATENT DOCUMENTS 36 16 649    11/1987 (DE) .

* cited by examiner

Primary Examiner—Brian Sircus
Assistant Examiner—Javaid Nasri
(74) Attorney, Agent, or Firm—Schiff Hardin & Waite

(57) ABSTRACT

Connection unit for connecting two units which are spatially removed from each other, has at least one connecting line and at least two fixtures for holding and leading the connecting lines, these fixtures being provided with elements which can be fixed in and loosened from mating components that fit the elements, and with arbitrary frequency.

5 Claims, 2 Drawing Sheets

CONNECTION UNIT FOR USE IN A MEDICAL WORKPLACE

BACKGROUND OF THE INVENTION

1. Field of the Invention

The present invention relates to a connection unit for connecting two units which are spatially removed from each other, the unit having at least one connecting line. The invention also relates to the use of such a connection unit in a medical workplace for connecting two spatially separated medical units.

2. Description of the Prior Art

The connection of two spatially separated units, such as the electrical connection of two electrically operated units by means of electrical cables, is well known. The electrical cables which connect the units are either laid permanently between the units (i.e., the cables can not be manually removed, or can be removed only with difficulty) or they are fixed against a wall with clamps, for example, or the cables are free (i.e. they do not have any mounts at all).

German OS 36 16 649 describes a cable harness which is provided for integration in a household device and which comprises cable bundles, which are joined to cable confiners at discrete points. The cable confiners, in the form of injected-molded plastic rings, are provided with fixing elements by means of which the cable harness can be fixed at walls of the household device, for example.

German PS 42 07 666, corresponding to U.S. Pat. No. 5,377,939, teaches a device for fixing structural elements which has at least two enclosure elements for fixing the structural elements. The enclosure elements can be fixed to an assembly surface by means of pin-shaped connecting elements which extend through the enclosure elements. Each pin-shaped connecting element has an expanding head at one end, which can be inserted into a locking element that is arranged in a bore of the assembly surface. The end of a connecting element situated opposite the expanding head is provided with a thread which engages a nut. A tightening of the nut effects a longitudinal displacement of the connecting element, thereby effecting the expansion of the locking element in the bore and thus fixing the device at the assembly surface. The enclosure elements are also held against each other, thereby fixing the structural elements between the enclosure elements.

In specific fields of application, for example in the operating room of a hospital, this fixed type of connection of two medical units can prove disadvantageous or unsuitable, to the extent that the course of the fixedly laid cable can not be adapted to different situations, for example, to the varied spatial orientation of the two medical units to be connected. Furthermore, due to their being fixed, the cables can be sterilized only with difficulty, if at all. Free cables are easier to sterilize and, due to their lack of being fixed, can (within certain limits) be adapted to varied situations with respect to their course, but they can not generally be held as desired relative to the units to be connected. The cables are therefore often located in the area of movement of people, where they have a disruptive effect.

SUMMARY OF THE INVENTION

It is an object of the present invention to provide a connection unit of the type initially described above which still allows the course of the connecting lines of the connection unit between two connected units to be modified easily.

This object is inventively achieved in a connection unit for connecting two units which are spatially removed from each other, having at least one connecting line and at least two fixtures for holding and guiding the connecting line, the fixtures having elements which can be repeatedly fixed (tightened) and loosened, with arbitrary frequency, mating components that match the elements, it being possible to displace the fixtures relative to one another even when a connecting line is accepted therein. By the fixtures of the connection unit, the connecting line (and, more commonly, connecting lines) of the connection unit are appropriately held and led, it being possible to fix the elements of the fixtures in the mating components cooperating with the elements such that the course of the connecting lines between two connected units can be influenced depending on the attachment point of the mating components, i.e., the course can be adapted to the particular situation for the two spatially separated units to be connected. The position the orientation and the attachment location of the fixtures can be modified without complications. The elements of the fixtures and the mating components for the elements are constructed such that the fixtures can be fixed in the mating components and loosened again by means of the elements with arbitrary frequency. If the connection unit is provided for the connection of two units in a sterile environment, for example, in an operating room of a hospital, then, on the basis of its inventive construction, the connection unit can be sterilized without complications and used in a sterile environment. Since the fixtures can be displaced relative to each other, the lengths of the connecting lines between two fixtures is adjustable.

Depending on the manner in which the course of the connecting lines between the units to be connected is to be influenced, two or more fixtures for holding and leading the connecting lines can be provided. The connecting lines usually have terminals at each end with which they can be connected to the units which are to be connected.

According to a variation of the invention, the fixtures have gripping handles. This is particularly advantageous if the connection unit is provided for the connection of two medical units, in an operating room, for example. When the connection unit has been sterilized completely, the connecting lines can be led as desired from one unit to the other by means of the gripping handles of the fixtures, without touching the lines directly, which would render them at least partly unsterile, and the elements of the fixtures can be fixed in corresponding mating components which are arranged at or in the region of the units.

In an embodiment of the invention, each fixture has a chamber for each connecting line for holding and leading the respective connecting lines, thereby improving the leading of the connecting lines, particularly in the mutual displacement of the fixtures.

According to a variation of the invention, connecting lines can be added to the fixtures and removed from them. In this way, the connection unit can be configured with connecting lines for different instances of use. According to a further variation of the invention, the connection unit has connecting lines in the form of electrical connecting cables and/or light waveguides and/or compressed air lines and/or gas lines.

The connection unit is preferably provided for utilization in a medical workplace having a device center for medical-technical devices, applicators of the medical-technical devices and a patient support apparatus. The connection unit thus connects the medical-technical devices to their applicators, so that, preferably, one apparatus, by means of its element, can be fixed at or in the region of the device center, and another apparatus, by means of its element, is fixed at or in the region of the patient support apparatus, in corresponding mating components. In this way, not only are the connecting lines between the device center and the applicators, which are usually arranged at or in the region of the patient support apparatus, appropriately led, but also the device center and the applicators are connected easily to one another.

In a further embodiment of the invention provides a number of mating components for accepting the elements of the fixtures are provided at or in the region of the patient support apparatus, so that the fixtures can be fixed relative to the patient support apparatus according to the respective treatment situation; i.e., the course of the connecting lines can be adapted by means of the fixtures according to the placement of the applicators at or around the patient support apparatus.

DESCRIPTION OF THE PREFERRED EMBODIMENTS

Figure 1:
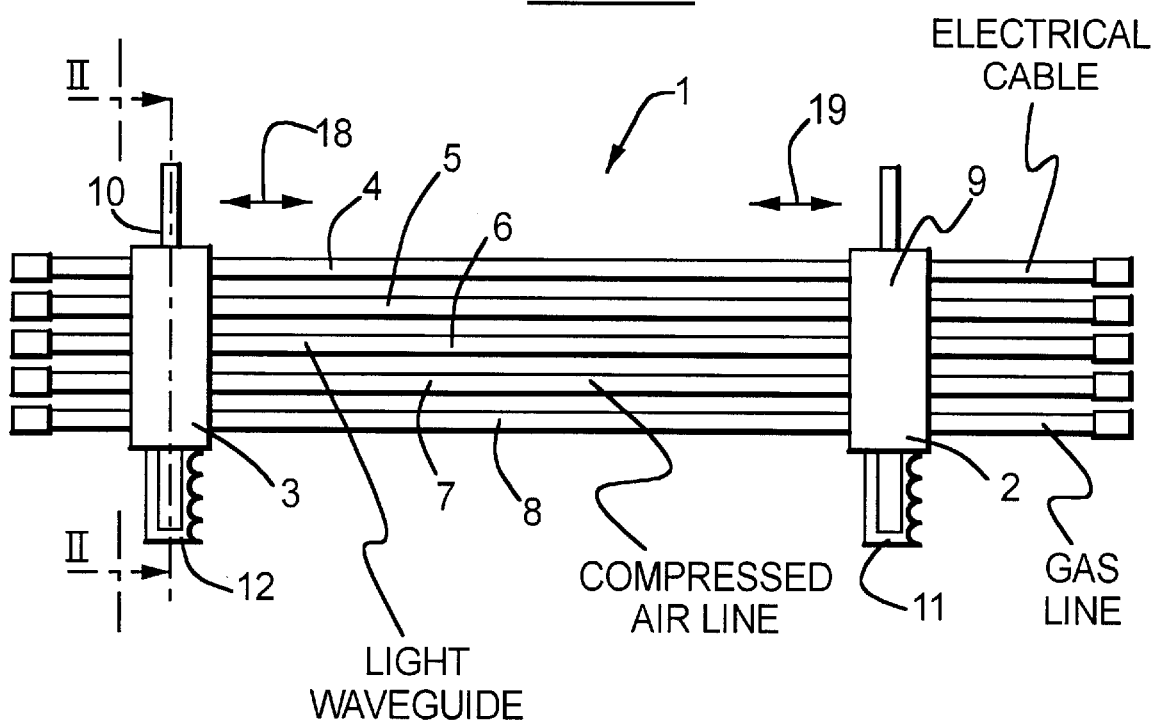
FIG. 1 shows a connection unit in accordance with the invention with two fixtures for holding and guiding connecting lines.

FIG. 1 depicts an inventive connection unit 1 for connecting two units (not illustrated) which are spatially removed from one another. In the case of the exemplary embodiment, the connection unit 1 has two fixtures 2, 3 for holding and leading five connecting lines 4 to 8. The fixtures 2, 3 are provided with elements 9, 10, which are constructed in the shape of a pin in the exemplary embodiment, these elements 9, 10 serving (as described below) for fixing the fixtures 2,3 in mating components that cooperate with the elements 9,10 of the fixtures 2, 3. The fixtures 2, 3 also each have a gripping handle 11, 12 so that the connection unit 1 that contains the fixture 2, 3 and the connecting lines 4 to 8 can be comfortably carried by a person (not illustrated).

The connecting lines 4 to 8 of the connection unit 1 are provided with terminal pieces (not detailed) at their ends, with which they can be connected to the units to be connected.

Figure 2:
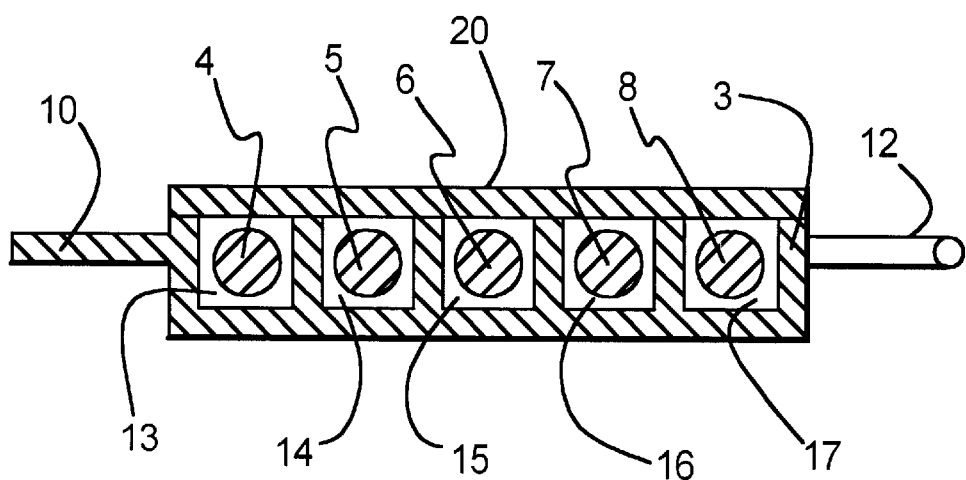
FIG. 2 shows the section II—II from FIG. 1.

FIG. 2 depicts the section II—II of the device 3 from FIG. 1. As can be seen in FIG. 2, each of the connecting lines 4 to 8 is allocated to a chamber 13 to 17 of the fixture 3. The connecting lines 4 to 8 are led loosely through the chambers 13 to 17. In this way, the fixtures 2, 3 can be mutually displaced, which is illustrated in FIG. 1 by the two double arrows 18, 19. The chambers 13 to 17 serve for the holding and leading of the connecting lines 4 to 8.

As illustrated in FIG. 2 for the fixture 3, each of the fixtures has a removable and recloseable cover 20, so that connecting lines can be removed from and added to the fixtures 2, 3. In this way, the connection unit 1 can be configured with different connecting lines for different applications. Thus, the fixtures 2, 3 need not necessarily have five chambers 13 to 17, each for a connecting line, but can have more or fewer chambers. Furthermore, the chambers need not have a square cross-section, but can also have another type of cross-section, such as a round cross-section. The connecting lines 4 to 8 can be electrical connecting cables and/or light waveguides and/or compressed air lines and/or gas lines.

Figure 3:
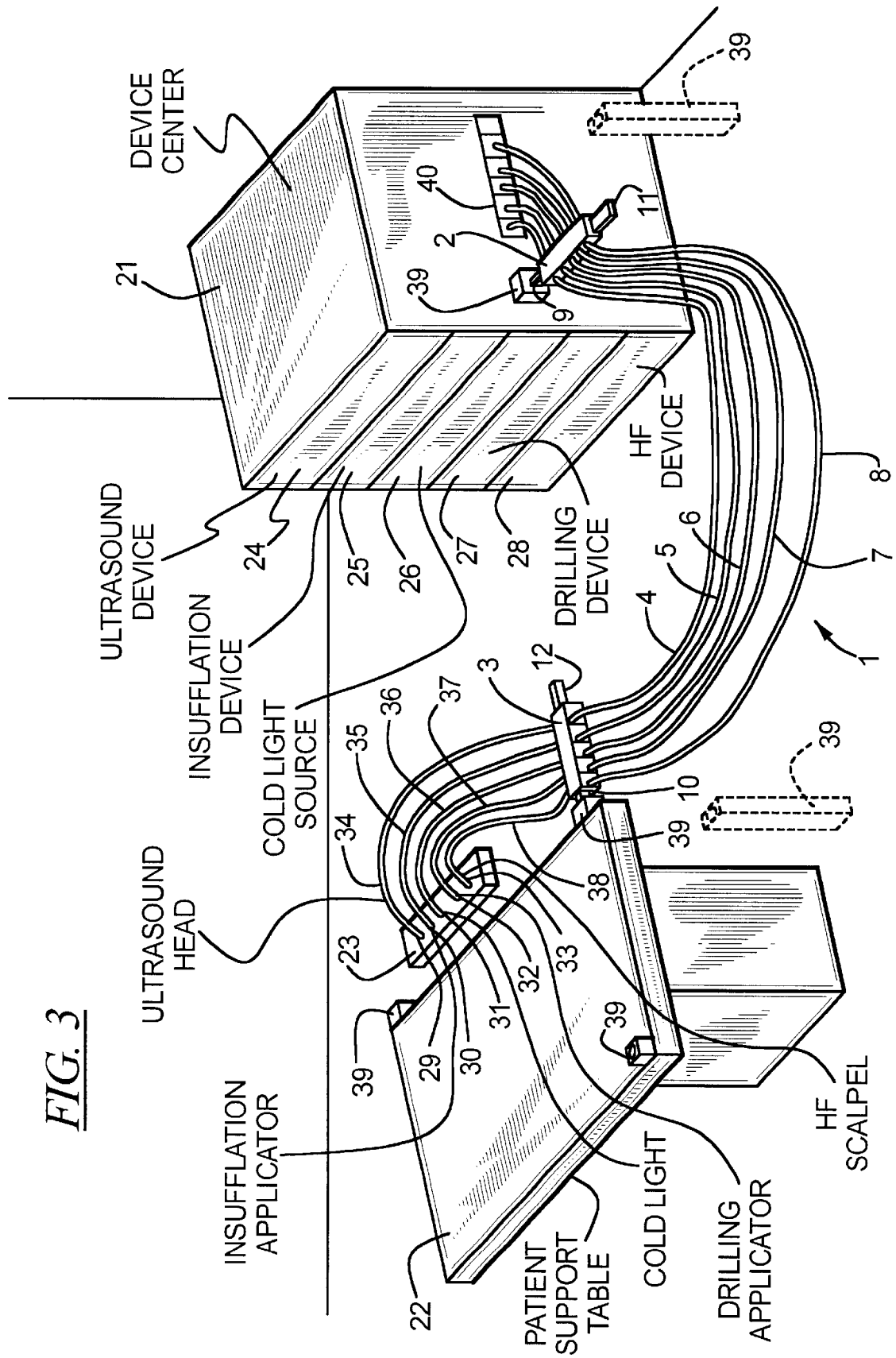
FIG. 3 shows a medical workplace with the inventive connection unit of FIG. 1.

As an example of a field of use for the inventive connection unit 1, FIG. 3 illustrates a medical workplace for minimally invasive surgery. The workplace has a patient support table 22, a device center 21 with medical-technical devices, which is spatially removed from the patient support table 22, and applicators of the medical-technical devices.

In the exemplary embodiment, the applicators are placed on a tray 23 which is arranged at the patient support table 22. The tray 23 can be varied with respect to its position at the patient support table 22. For example, the tray 23 can be attached at various points at the tabletop of the patient support table 22.

In the exemplary embodiment, there is an ultrasound device 24, an insufflation device 25, a cold-light source 26, a drilling device 27 and a HF device 28 arranged in the device center 21. On the tray 23, the applicators appertaining to the medical-technical devices 24 to 28 are arranged, these being in the present case an ultrasound head 29, an insufflation applicator 30, a cold light 31, a drilling applicator 32 and a HF scalpel 33. The applicators 29 to 33 have terminal leads 34 to 38, respectively (terminals not illustrated).

In the exemplary embodiment, the applicators 29 to 33, which are provided with the terminal leads 34 to 38, are connected to their associated medical-technical devices 24 to 28, which are arranged in the device center 21, via the inventive connection unit 1 illustrated in FIG. 1.

The fixture 2 of the connection unit 1 is fixed with its pin-shaped element in a mating component 39a, which is secured at the device center 21 and which fits the pin-shaped element 9. In the exemplary embodiment, the fixing occurs by means of clamping the element 9 in the mating component 39a, the clamping means, such as a clamping screw or a wire clamp, not being illustrated. The fixture 3 of the connection unit 1 is fixed with its pin-shaped element 10 in a mating component 39b, which corresponds to the mating component 39a but is secured at the patient support table 22. The fixing occurs as in the case of fixture 2.

It is advantageous that, by means of the gripping handles 11, 12 of the fixtures 2, 3, a person (not illustrated in FIG. 3) who is not sterilized can position the connection unit 1, which has been sterilized for use in the operating room and can fix it in the mating components 39a and 39b, without rendering the sterilized connecting lines 4 to 8 of the connection unit 1 unsterile by direct contact.

To establish the connection between the medical-technical devices 24 to 28 and their applicators 29 to 33, which are located on the tray 23, the person first fixes the fixture 2 with its element 9 in the mating component 39a which is arranged at the device center 21, and then fixes the fixture 3 with its element 10 in the mating component 39b which is arranged at the patient support table 22. This may occur by the displacement of the fixture 3 with respect to the fixture 2 in order to adapt the line lengths of the connecting lines 4 to 8 to the required distance between the fixtures 2 and 3. In order to prevent the connecting lines 4 to 8 from slipping out of the fixtures 2 3, the terminals at the ends of the connecting lines 4 to 8 are constructed larger than the chambers 13 to 17 of the fixtures 2,3. Subsequent to the fixing of the fixtures 2, 3, the non-sterilized person can contact the terminals of the connecting lines 4 to 8 with corresponding terminals at a termination panel 40 of the device center 21. The terminals of the termination panel 40 of the device center 21 are connected internally to the corresponding devices 24 to 28. The connection of the other terminals of the connection lines 4 to 8 to the terminals of the connection lines 34 to 38 of the applicators 29 to 33 need not occur by a sterilized person, however. In this way, it is guaranteed that the connection lines 4 to 8 remain sterile as required in the region of the patient support table 22. The regions of the connecting lines 4 to 8 which run from the patient support table 22 to the device center 21 can certainly run on the floor and can be unsterile.

In the exemplary embodiment, the connecting line 4 is an electrical cable which connects the ultrasound head 29 to the ultrasound device 24. The connecting line 5 is a gas line which connects the insufflation applicator 30 to the insufflation device 25. The connecting line 6 is a light waveguide which connects the cold-light 31 to the cold-light source 26. The connecting line 7 is a compressed air line which connects the drill applicator 32 to the drilling device 27, and the connecting line 8 is an electrical connecting cable which connects the HF scalpel 33 to the HF device 28.

As mentioned above, depending on the applicators required at the patient support table 22, connecting lines can be removed from, or added to the connection unit 1, so that the connection unit 1 can be adapted to the corresponding operating situation with respect to the required connection lines.

In addition, a number of mating components can be attached to the patient support table 22, as indicated by a further mating component 39c in which counterparts the fixture 3 of the connection unit 1 can be fixed. In this way, the connection unit 1, or the fixture 3, can be situated relative to the patient support table 22 as corresponds to the respective treatment situation. The arrangement of the mating components 39a and 39c (and others) at the patient support table 22 can differ from the arrangement depicted in FIG. 3.

In addition, further mating components, represented by mating components 39d, 39e than those which are illustrated in FIG. 3, can be provided which need not necessarily be arranged at the patient support table 22, for the corresponding fixing of the fixture 3 of the connection unit 1 relative to the patient support table 22. The same applies to the mating component 39b arranged at the device center 21. Mating components 39d and 39e (dashed line) are illustrated in FIG. 3 as examples next to the patient support table 22 and the device center 21, respectively.

Beyond this, the connection unit 1 can also include more than those fixtures 2, 3 and mating components 39a through 39e which are illustrated in the FIGS. 1 and 3, in order to be able to influence the course of the connecting lines between the units to be connected in an appropriate and desirable manner by the corresponding fixing of the elements of the fixtures in the mating components.

The inventive connection unit has been described in connection with a medical workplace, however, the use of the connection unit is not limited to medical fields of application.

Although modifications and changes may be suggested by those skilled in the art, it is the intention of the inventors to embody within the patent warranted hereon all changes and modifications as reasonably and properly come within the scope of their contribution to the art.

What is claimed is:

1. A connection unit for connecting two units which are spatially separated from each other, comprising:
   at least one connecting line;
   at least a first fixture and a second fixture for holding and leading said at least one connecting line;
   said first fixture having a first mating element adapted for repeatedly mating with and releasing said first fixture;
   said second fixture having a second mating element adapted for repeatedly mating with and releasing said second fixture;
   said first fixture having at least one chamber therein through which said connection line loosely proceeds, and said second fixture having at least one chamber therein through which said connection line loosely proceeds; and
   said first and second fixtures being mutually displaceable relative to each other while containing said at least one connecting line therein to adjust a length of said at least one connecting line between said first and second fixtures.

2. The connection unit as claimed in claim 1 further comprising a gripping handle on said first fixture and a gripping handle on said second fixture.

3. The connection unit as claimed in claim 1 further comprising more than one connecting line, and wherein each of said first and second fixtures comprises more than one chamber for individually holding and leading said connecting lines, respectively.

4. The connection unit as claimed in claim 1 wherein each of said first and second fixtures has a removable portion allowing connection lines to be added and removed therefrom.

5. The connection unit as claimed in claim 4 wherein said at least one connecting line is selected from the group consisting of electrical cables, light waveguides, compressed air lines, and gas lines.

* * * * *